US010327757B1

(12) United States Patent
Martin et al.

(10) Patent No.: US 10,327,757 B1
(45) Date of Patent: Jun. 25, 2019

(54) SURGICAL SYSTEM WITH ENDOSCOPE AND SUTURING INSTRUMENT

(71) Applicant: Ethicon Endo-Surgery, LLC, Guaynabo, PR (US)

(72) Inventors: David T. Martin, Milford, OH (US); Frederick E. Shelton, IV, Hillsboro, OH (US)

(73) Assignee: Ethicon LLC, Guaynabo, PR (US)

( * ) Notice: Subject to any disclaimer, the term of this patent is extended or adjusted under 35 U.S.C. 154(b) by 642 days.

(21) Appl. No.: 14/741,616

(22) Filed: Jun. 17, 2015

(51) Int. Cl.
 A61B 17/04 (2006.01)
 A61B 17/062 (2006.01)
 A61B 17/00 (2006.01)

(52) U.S. Cl.
 CPC .... *A61B 17/0469* (2013.01); *A61B 17/00234* (2013.01); *A61B 17/0482* (2013.01); *A61B 17/062* (2013.01); *A61B 2017/00296* (2013.01); *A61B 2017/00477* (2013.01); *A61B 2017/0498* (2013.01)

(58) Field of Classification Search
 CPC . A61B 17/0482; A61B 17/0483; A61B 17/04; A61B 17/0469; A61B 2017/047; A61B 2017/0472; A61B 2017/003; A61B 2017/00318; A61B 2017/00323; A61B 2017/00327; A61B 1/008; A61M 25/0133; A61M 25/0136; A61M 25/0147; A61M 25/0138; A61M 25/0141; A61M 25/0144; A61M 2025/015; A61M 2017/00327; A61M 2017/00323
 See application file for complete search history.

(56) References Cited

U.S. PATENT DOCUMENTS

| 5,358,478 | A | * | 10/1994 | Thompson | A61M 25/0136 604/528 |
| 5,891,088 | A | * | 4/1999 | Thompson | A61M 25/0136 604/524 |
| 5,921,956 | A | * | 7/1999 | Grinberg | A61B 1/0052 600/146 |
| 6,159,224 | A | * | 12/2000 | Yoon | A61B 17/0469 606/139 |
| 6,719,764 | B1 | * | 4/2004 | Gellman | A61B 17/0469 606/144 |
| 7,615,060 | B2 | | 11/2009 | Stokes et al. | |
| 8,702,732 | B2 | | 4/2014 | Woodard et al. | |
| 9,168,037 | B2 | | 10/2015 | Woodard et al. | |
| 9,357,998 | B2 | | 6/2016 | Martin et al. | |
| 9,375,212 | B2 | | 6/2016 | Martin et al. | |
| 9,474,522 | B2 | | 10/2016 | Deck et al. | |
| 2003/0233104 | A1 | * | 12/2003 | Gellman | A61B 17/0469 606/139 |

(Continued)

*Primary Examiner* — Christopher L Templeton
(74) *Attorney, Agent, or Firm* — Frost Brown Todd LLC

(57) ABSTRACT

A surgical instrument includes a body, at least one user input feature, an elongate shaft extending from the body along a longitudinal axis, and a needle applier coupled to the elongate shaft. The needle applier further includes a needle and a drive assembly coupled to the needle. The drive assembly is configured to rotate the needle along an orbital path about a rotation axis that is transverse to the longitudinal axis, in response to an actuation of the user input feature. The surgical instrument further includes a coupler operable to couple the surgical instrument to an endoscope for use in, among other surgical procedures, gastric reduction procedures.

16 Claims, 15 Drawing Sheets

(56) References Cited

U.S. PATENT DOCUMENTS

| | | | |
|---|---|---|---|
| 2006/0282098 A1* | 12/2006 | Shelton, IV | A61B 1/00087 606/144 |
| 2007/0167978 A1* | 7/2007 | Yamamoto | A61B 17/0469 606/205 |
| 2007/0239177 A1* | 10/2007 | Stokes | A61B 17/0469 606/144 |
| 2008/0300462 A1* | 12/2008 | Intoccia | A61B 1/00071 600/146 |
| 2009/0312773 A1* | 12/2009 | Cabrera | A61B 17/0469 606/144 |
| 2009/0312775 A1* | 12/2009 | Gilkey | A61B 1/018 606/147 |
| 2010/0121147 A1* | 5/2010 | Oskin | A61B 1/0051 600/118 |
| 2011/0152891 A1* | 6/2011 | McLawhorn | A61B 17/0625 606/145 |
| 2012/0232567 A1* | 9/2012 | Fairneny | A61B 17/0469 606/147 |
| 2012/0271327 A1* | 10/2012 | West | A61B 1/018 606/144 |
| 2015/0112134 A1* | 4/2015 | Suehara | A61B 1/00082 600/109 |
| 2015/0133967 A1* | 5/2015 | Martin | A61B 17/0482 606/144 |

\* cited by examiner

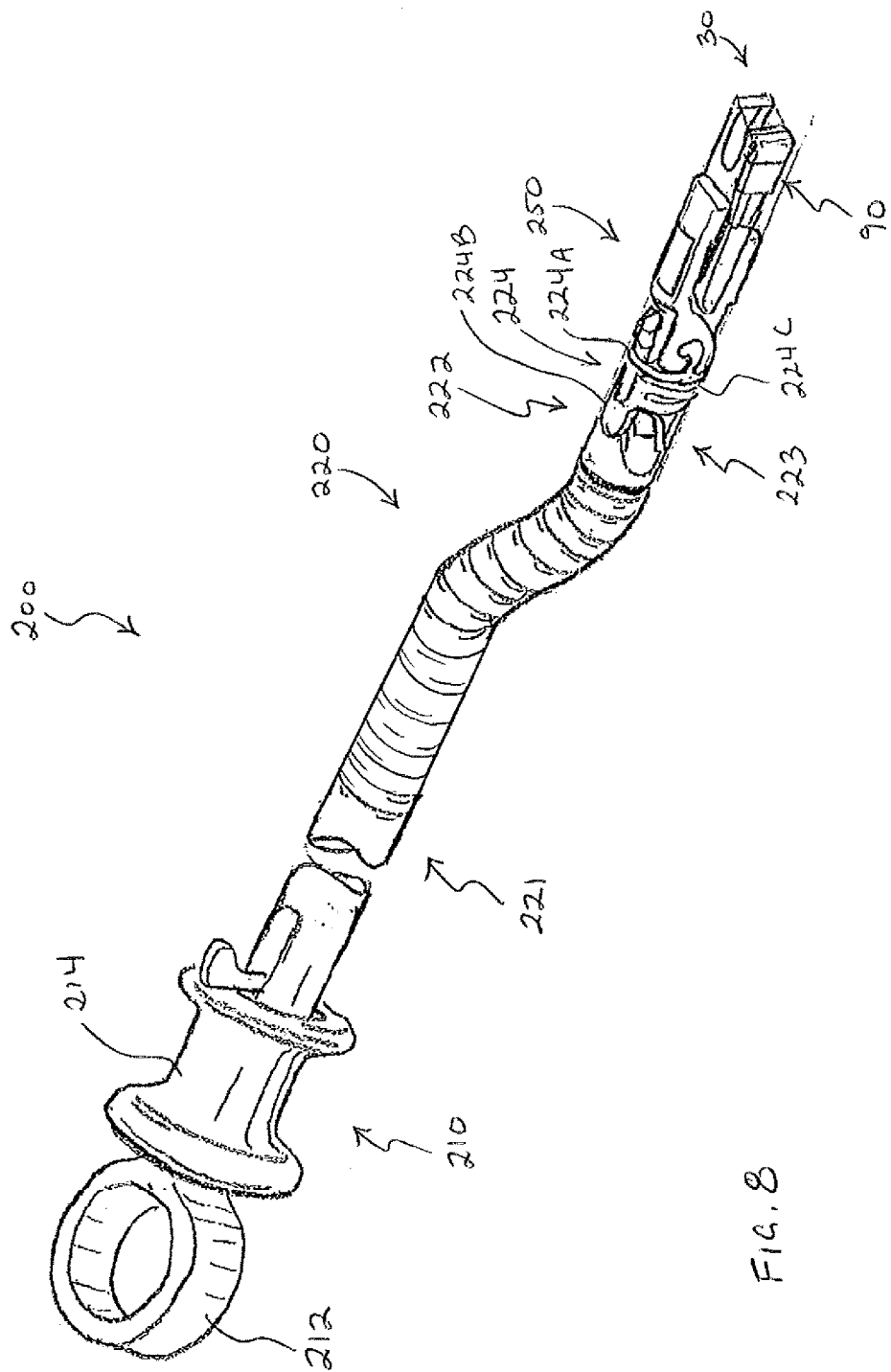

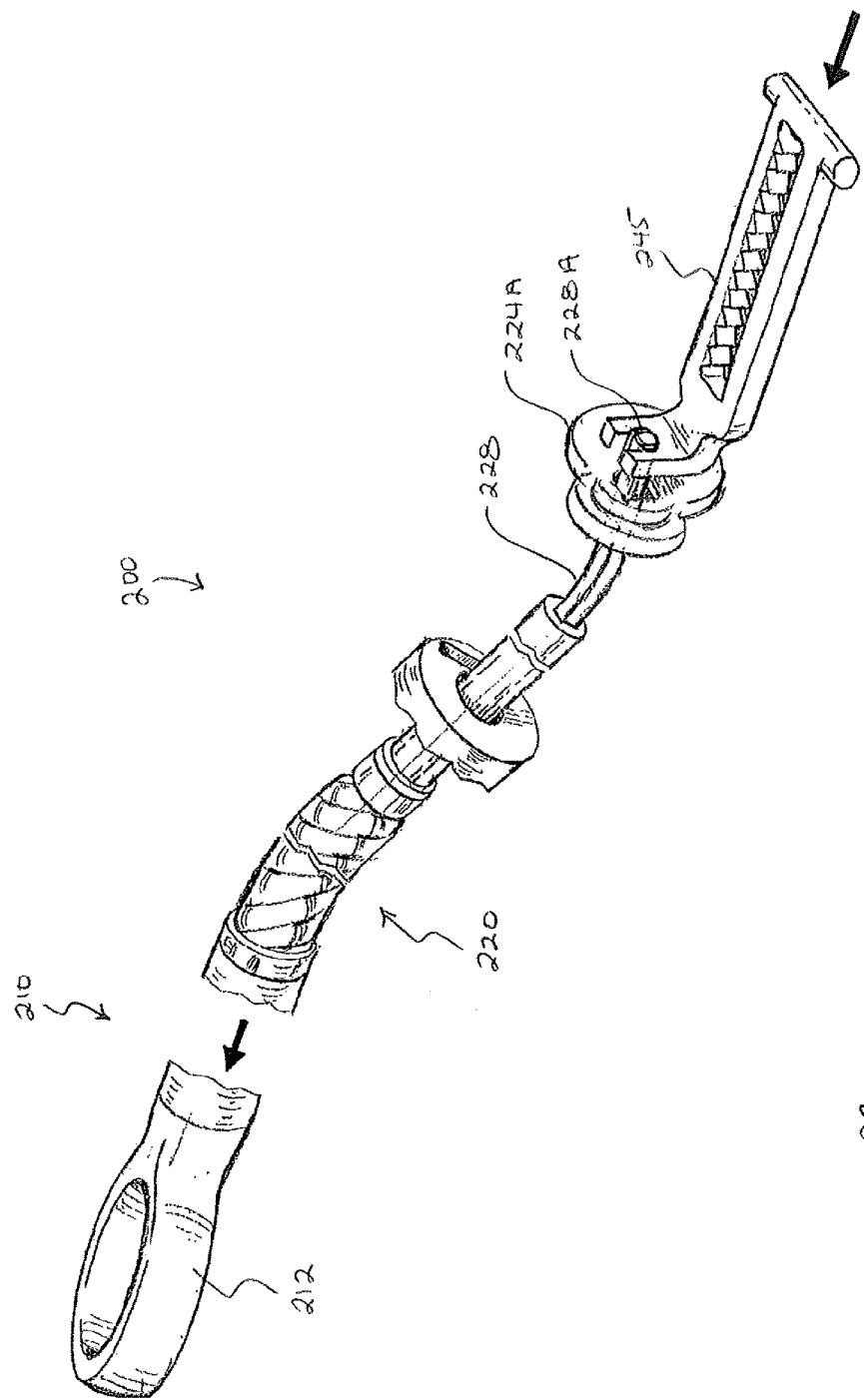

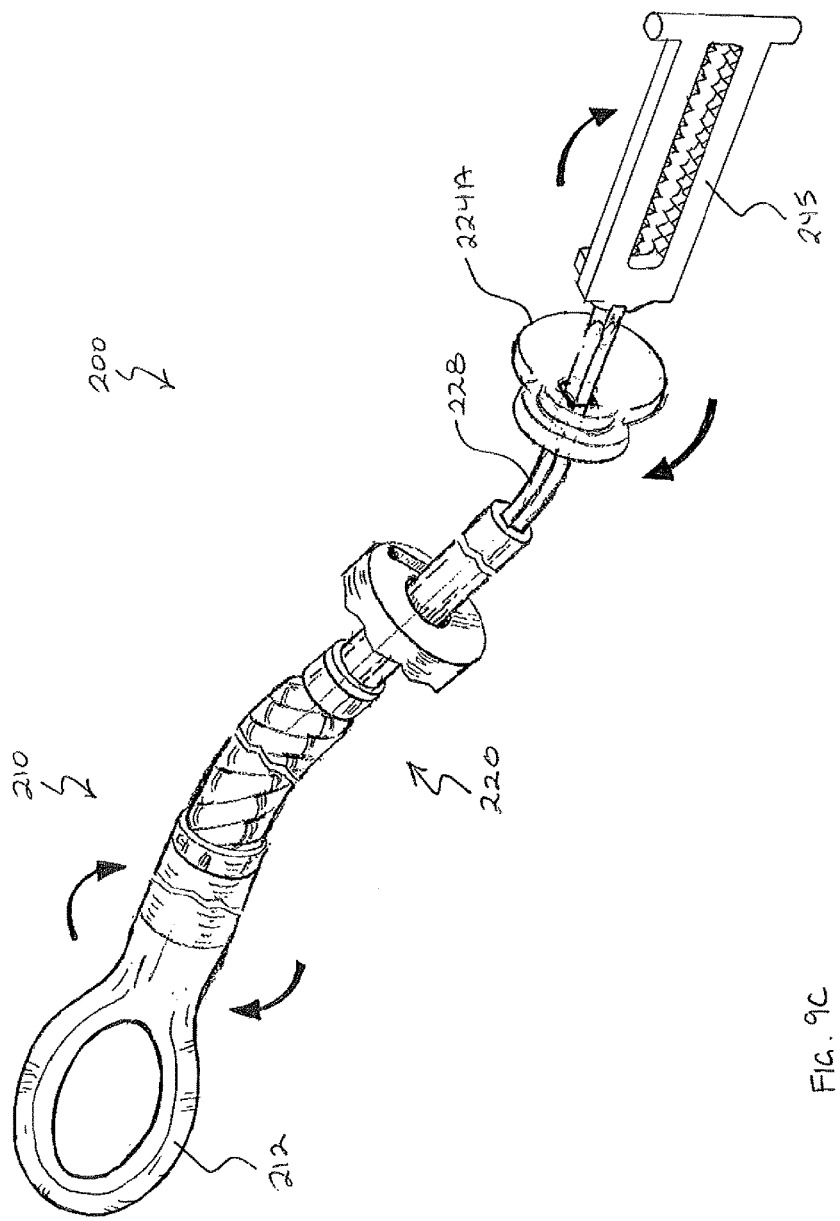

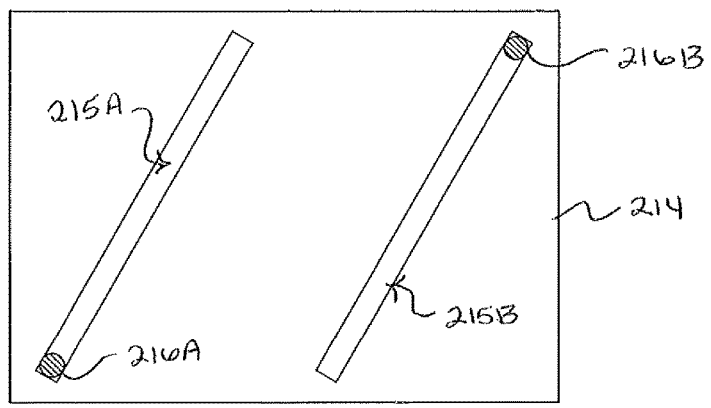
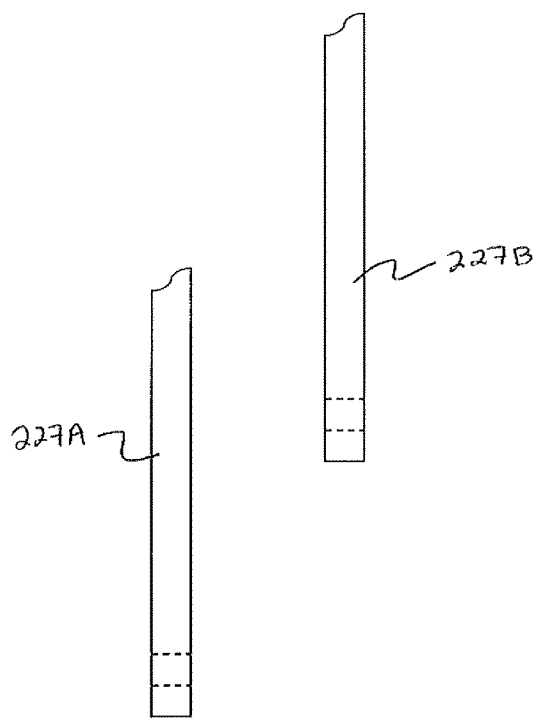
FIG. 11A

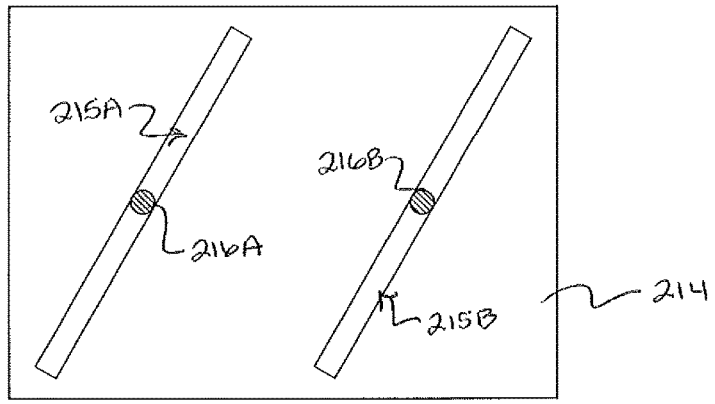
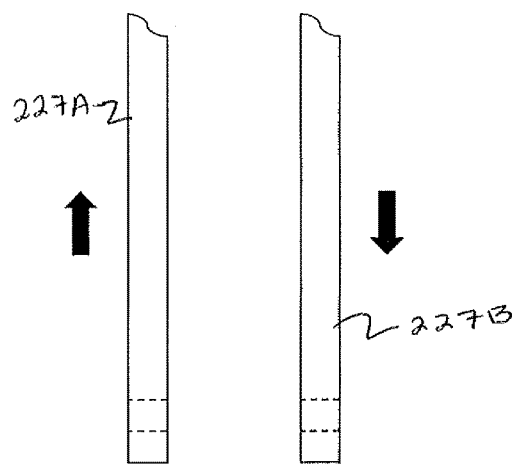
FIG. 11B

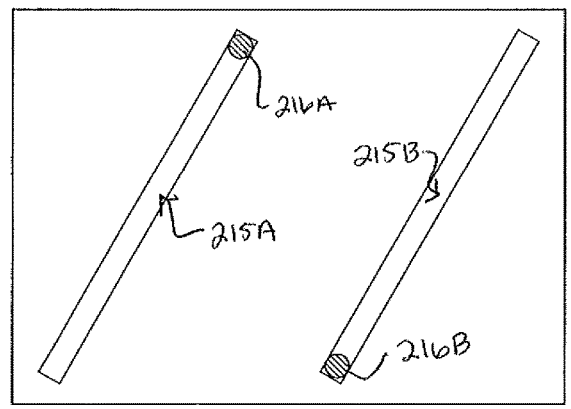
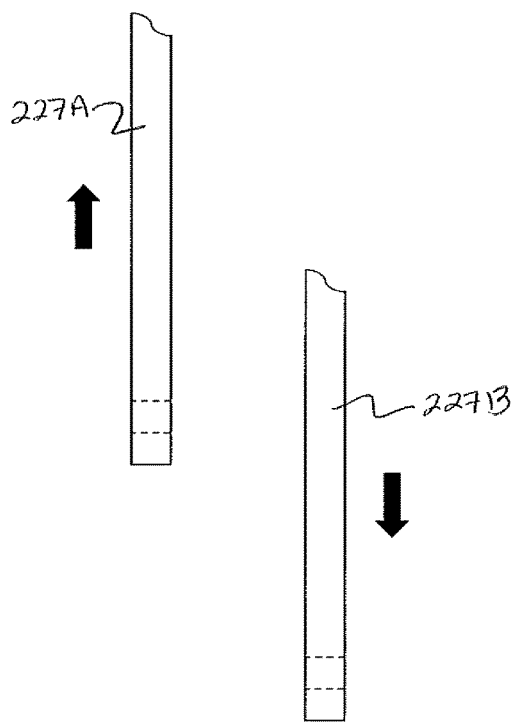
FIG. 11C

SURGICAL SYSTEM WITH ENDOSCOPE AND SUTURING INSTRUMENT

BACKGROUND

Sutures may be used in a wide variety of surgical procedures. Manual suturing may be accomplished by the surgeon using a fine pair of graspers to grab and hold a suture needle, pierce the tissue with the needle, let go of the needle, and re-grasp the needle to pull the needle and accompanying suture thread through the tissues to be sutured. Such needles may be curved with the suture attached to the trailing end of the needle.

Some surgical instruments automate at least part of the suturing procedure. Examples of automated suturing instruments are described in U.S. Pat. No. 8,702,732, entitled "Laparoscopic Suturing Instrument with Dual-Action Needle Graspers," issued Apr. 22, 2014, the disclosure of which is incorporated by reference herein; U.S. Pub. No. 2011/0313433, entitled "Laproscopic Suture Device with Asynchronous In-Line Needle Movement," published Dec. 22, 2011, issued as U.S. Pat. No. 9,168,037 on Oct. 27, 2015, the disclosure of which is incorporated by reference herein; U.S. Pub. No. 2014/0171970, entitled "Circular Needle Applier with Articulating and Rotating Shaft," published Jun. 19, 2014, issued as U.S. Pat. No. 9,357,998 on Jun. 7, 2016, the disclosure of which is incorporated by reference herein; and U.S. patent application Ser. No. 14/297,993, entitled "Jawed Cartridge receiving assembly for Needle Cartridge," filed Jun. 6, 2014, issued as U.S. Pat. No. 9,474,522 on Oct. 25, 2016, the disclosure of which is incorporated by reference herein.

While various kinds of suturing instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 8 depicts a perspective view of the instrument of FIG. 7 without the endoscope;

FIG. 9B depicts a perspective view of the internal distal head control components of FIG. 9A, with the distal end of the instrument moved to a proximal longitudinal position;

FIG. 9C depicts a perspective view of the internal distal head control components of FIG. 9A, with the distal end of the instrument rotated to a second rotational position;

FIG. 11A depicts a top view of some of the internal articulation control components of FIG. 10, with an articulation control knob of the instrument in a first rotational position and with articulation bands of the instrument in a first position relative to one another;

FIG. 11B depicts a top view of some of the internal articulation control components of FIG. 10, with the rotation knob of FIG. 11A moved to a second rotational position so as to drive the articulation bands of FIG. 11A in opposing directions relative to one another so as to drive the articulation bands to a second position relative to one another; and FIG. 11C depicts a top view of some of the internal articulation control components of FIG. 10, with the rotation knob of FIG. 11A moved to a third rotational position so as to drive the articulation bands of FIG. 11A in opposing directions relative to one another so as to drive the articulation bands to a third position relative to one another.

Figure 1:
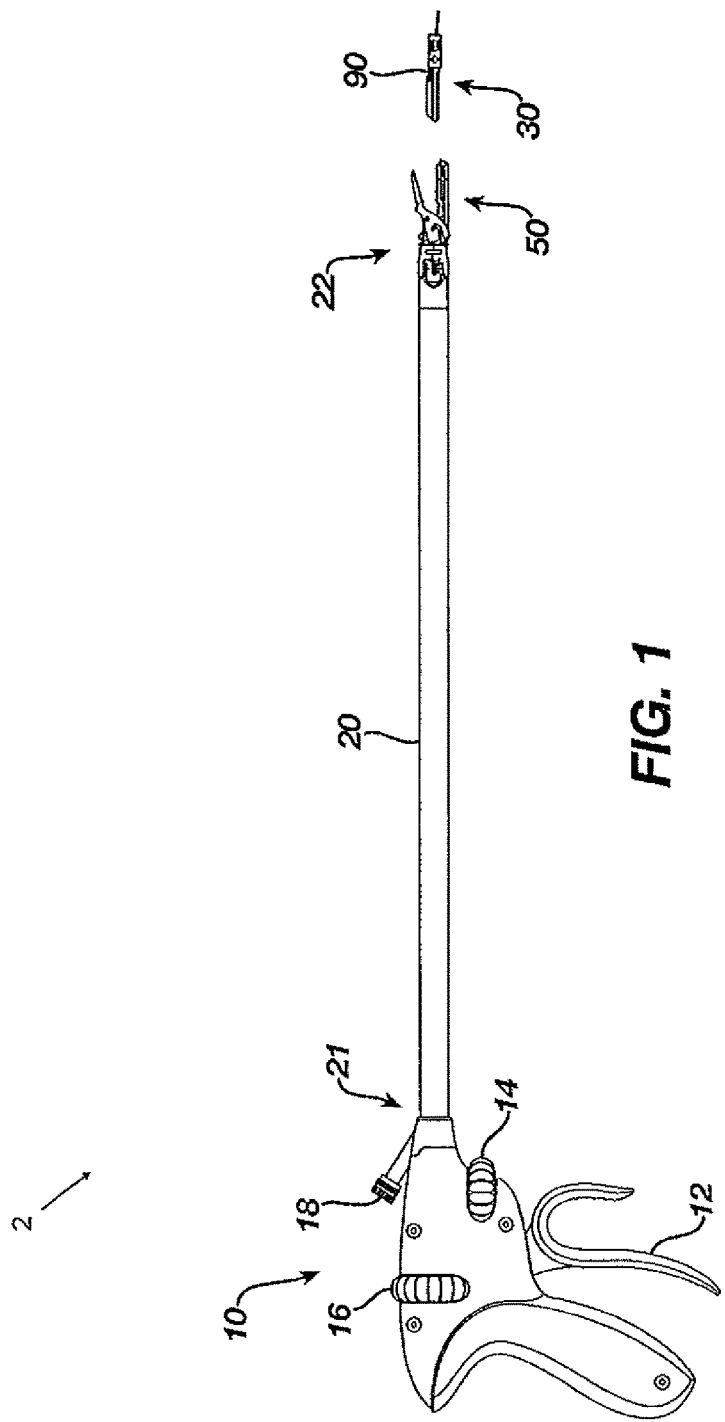
FIG. 1 depicts a side view of an exemplary surgical suturing instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Surgical Suturing Instrument

FIG. 1 illustrates an example of a surgical suturing instrument (2). Instrument (2) comprises a handle assembly (10), an elongate shaft (20), and a cartridge receiving assembly (50), which is operable to receive a needle applier cartridge (30). Shaft (20) has a proximal end (21), a distal end (22), and a longitudinal axis extending therebetween. Handle assembly (10) is connected to the proximal end (21) of the shaft (20). In this example handle assembly (10) is a manual pistol grip handle. However, a variety of other manual actuators could also be used, including but not limited to a scissor grip handle, a syringe grip handle, endoscopic rotary knobs, and the like. Handle assembly (10) could also take the form of a robotic interface, such as a DAVINCI puck, or a housing comprising gears or pulleys, servomechanisms, and the like.

Needle applier cartridge (30) is connected to the distal end (22) of shaft (20) via cartridge receiving assembly (50). Needle applier cartridge (30) is operable to rotate an arced needle in a circular path enabling a surgeon to selectively apply sutures. In some alternative versions, needle applier cartridge (30) is integral with shaft (20) and handle assembly (10) as a unitary disposable instrument intended for a single surgical procedure. Needle applier cartridge (30) may also be integral with shaft (20) and handle assembly (10) as a reusable instrument. Optionally, as illustrated here, needle applier cartridge (30) may be provided in a disposable cartridge body (90) and shaft (20) includes cartridge receiving assembly (50) to releasably hold cartridge body (90). In some such versions, shaft (20) and handle assembly (10) may also be disposable or reusable. Versions with reusable components are intended to be cleaned, sterilized, and reused for a multiple surgical procedures, and may include a flush port (18) to facilitate cleaning. The preferable life cycle of a reusable instrument is at least 50 operations, more preferably at least 150 operations, and most preferably at least 200 operations. Reusable components may be built using materials that can withstand autoclave sterilization temperatures of at least 135 degrees Celsius, although low temperature materials can also be used with low temperature sterilization techniques known in the art.

A first input (12), shown here as a trigger that pivots between opened and closed positions, may be used to selectively actuate needle applier cartridge (30). The trigger may be spring biased to return the trigger to its open position. A second input (14), shown here as a rotary knob, may be used to selectively articulate shaft (20). A third input (16), shown here as a rotary knob, may be used to selectively rotate needle applier cartridge (30) about shaft (20). Of course, the number, type, configuration, and operation of inputs (12, 14, 16) may vary.

Figure 2A:
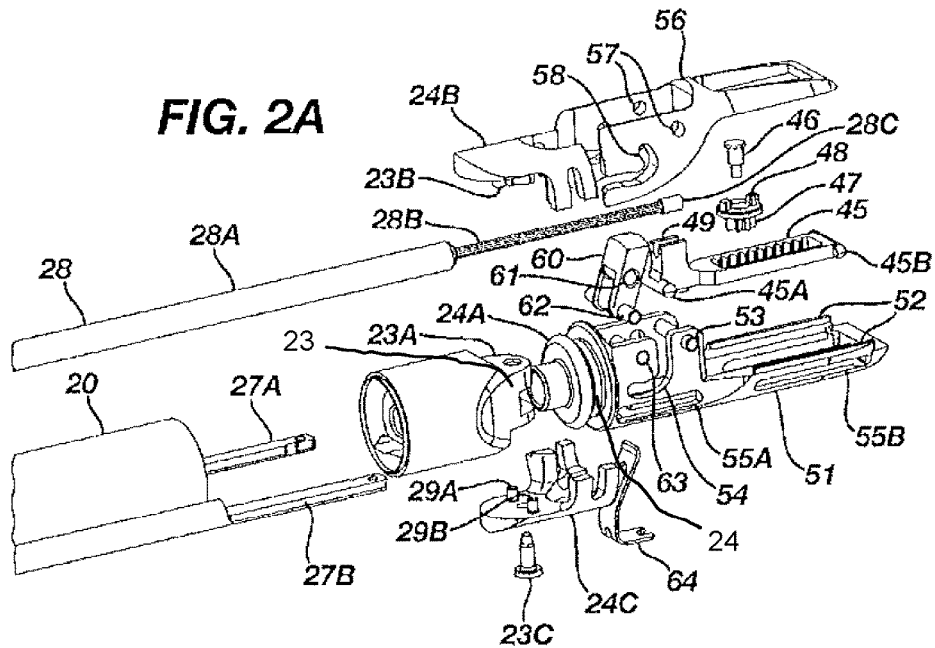
FIG. 2A depicts a top perspective exploded view of a cartridge receiving assembly of the instrument of FIG. 1.
Figure 2B:
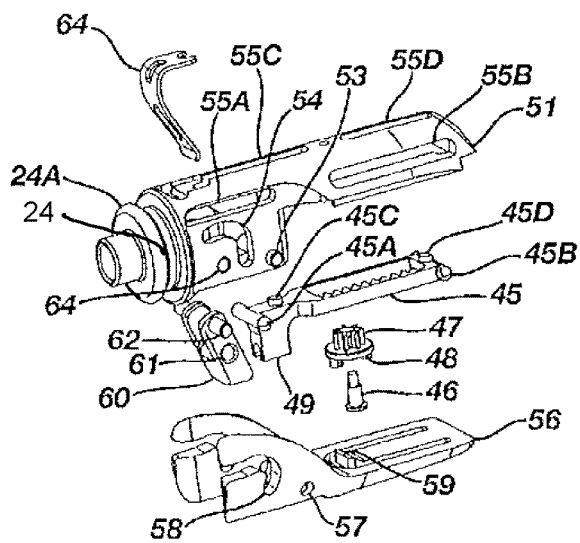
FIG. 2B depicts a bottom perspective exploded view of the cartridge receiving assembly of FIG. 2A.

FIGS. 2A-2B illustrate exploded views of cartridge receiving assembly (50) of the present example. Distal end (22) of shaft (20) comprises an articulation joint (23) and a rotational bearing (24). Articulation joint (23) includes a knuckle (23A) that receives pins (24B, 24C), which are connected to bearing supports (24B, 23C). Thus, pins (23B, 2C) define the pivoting axis for articulation joint (23), enabling cartridge receiving assembly (50) to articulate left and right relative the shaft (20), away from the longitudinal axis defined by shaft (20). Rods (27A, 27B) are operably connected to articulation joint (23). In this example, rods (27A, 27B) extend through shaft (20), through knuckle (23A), and connect to pins (29A, 29B) on bearing support (24C). Rods (27A, 27B) are operatively connected to rotary knob (14) to opposingly push and pull rods (27A, 27B). In other words, rotary knob (14) is operable to drive rods (27A, 27B) at the same time in opposite longitudinal directions, such that rod (27A) will translate distally while rod (27B) translates proximally; and such that rod (27B) will translate distally while rod (27A) translates proximally. Because pins (29A, B) are laterally spaced from the pivoting axis, the simultaneous push and pull action will in turn articulate cartridge receiving assembly (50) about joint (23) relative to shaft (20).

Rotational bearing (24) is positioned distal to articulation joint (23). Bearing (24) includes a circumferential flange (24A) that is captured between the bearing supports (24B, 24C) such that the flange (24A) can rotate relative the bearing supports (24B, 24C) and enabling unbounded rotation of cartridge receiving assembly (50) relative shaft (20) about the longitudinal axis defined by shaft (20). A drive rod (28) extends through shaft (20). In this example, drive rod (28) comprises a proximal rigid portion (28A) and a distal bendable portion (28B) that are fixedly connected to one another. Bendable portion (28B) extends through articulation joint (23) and through bearing (24); distal end (28C) is fixedly connected to a mount (49) on a rack (45).

Rack (45) reciprocates longitudinally in lower jaw (51) with followers (45A, 45B, 45C, 45D) constrained in tracks (55A, 55B, 55C, 55D), respectively. Tracks (55A, 55B, 55C, 55D) open through lower jaw (51), providing fluid passages to the internal components within the lower jaw (51), thus facilitating easier cleaning. A pinion (47) is mounted to lower jaw (51) by the pin (46) in the rack (45) such that longitudinal reciprocation of the rack (45) is converted into rotational reciprocation of pinion (47). A key (48) communicates the reciprocating rotation to a rotary input (94) in cartridge body (90), which in turn actuates needle applier cartridge (30).

Drive rod (28) is operatively connected to first input (12) and to third input (16). Actuation of first input (12) will impart axial push and pull loads on drive rod (28) to longitudinally reciprocate rack (45) and thereby actuate needle applier cartridge (30). Actuation of third input (16) will impart a rotational load on drive rod (28) thus rotating cartridge receiving assembly (50) about bearing (24) relative to shaft (20). Accordingly, a single drive rod (28) operates to both actuate needle applier cartridge (30) as well as control distal rotation of needle applier cartridge (30) about the longitudinal axis of shaft (20). By consolidating dual functions with a single drive rod (28), the number of components is reduced, and more space is provided in the shaft (20), which may make the device less expensive to manufacture and easier to clean.

Cartridge receiving assembly (50) is dimensioned and adapted to receive and hold cartridge body (90). As shown in FIGS. 2A-2B, cartridge receiving assembly (50) of this example has upper and lower jaws (56, 51) that are operable to transition between an open configuration and a closed configuration. In the closed configuration, jaws (56, 51) are operable to receive and retain cartridge body (90). In the open configuration, jaws (56, 51) are operable to release cartridge body (90). In the present example, lower jaw (51) is stationary and upper jaw (56) pivots. Alternatively, the arrangement could be reversed, or in some versions both jaws (56, 51) could pivot. Lower jaw (51) has two laterally offset longitudinal rails (52) that are dimensioned and adapted to receive cartridge body (90). Rails (52) help longitudinally align cartridge body (90) in cartridge receiving assembly (50) and laterally retain cartridge body (90) in jaws (51, 56). Upper jaw (56) pivots relative lower jaw (51) about a pin (53) that is received in holes (57). A tooth (59) is resiliently oriented downwardly from upper jaw (56) toward lower jaw (51) with a ramped distal face and a stepped proximal face. Tooth (59) is dimensioned and adapted to latch with cartridge body (90) and longitudinally retain cartridge body (90) in jaws (51, 56). Tooth (59) deflects by virtue of a resilient cantilevered arm extending proximally from the distal end of upper jaw (56). In this example, tooth (59) and the cantilevered arm are monolithic with upper jaw (56), thus reducing the number of components and moving pieces, which may make the device less expensive to manufacture and easier to clean.

A button (60) is operable to open and close jaws (51, 56). While button (60) could be placed on or near the handle assembly (10) in some versions, in this example button (60) is positioned adjacent cartridge receiving assembly (50), which eliminates a linkage in shaft (20) thus creating space in shaft (20) and making the device less expensive and easier to clean. The action of button (60) may vary, but in this example button (60) pivots relative to lower jaw (51) about a pin (63) that is received hole (61). A follower (62) is received by cam slots (54, 58). Pivoting button (60) proximally will open jaws (51, 56), while pivoting button (60) distally will close jaws (51, 56). A spring (64) engages and biases button (60) distally. By pulling button (60) proximally, follower (62) will drive cam slot (58) to open upper jaw (56). When button (60) is released, spring (64) will resiliently drive button (60) distally to close upper jaw (56).

Figure 3A:
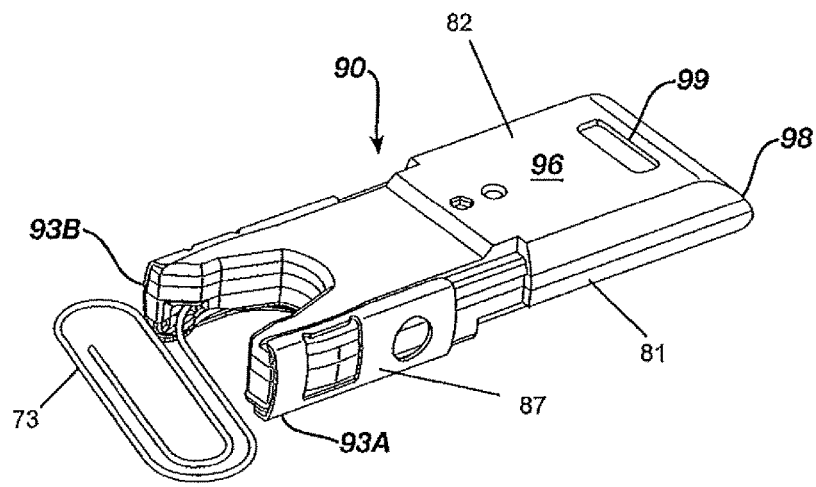
FIG. 3A depicts a top perspective view of an exemplary cartridge configured for receipt in the cartridge receiving assembly of FIG. 2A.
Figure 3B:
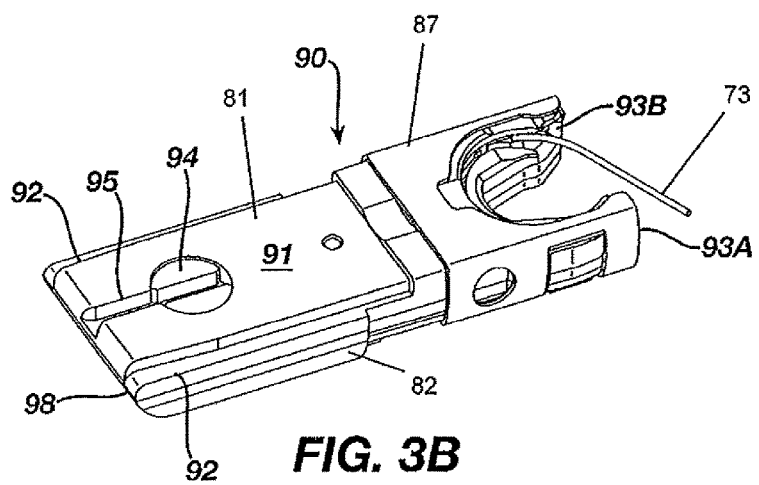
FIG. 3B depicts a bottom perspective view of the cartridge of FIG. 3A.

FIGS. 3A-3B illustrate cartridge body (90) of the present example in greater detail. A lower face (91) of cartridge body (90) is adapted to engage lower jaw (51); and an upper face (96) to engage upper jaw (56). Poke-yoke features on cartridge body (90) prevent improper insertion of cartridge body (90) into cartridge receiving assembly (50), but also contribute to the aesthetic appearance of cartridge body (90). For instance, lower face (91) has a pair of longitudinal notched shoulders (92) that are dimensioned to interface and mate with rails (52). In this example, notched shoulders (92) are shaped as a stepped rabbet, but a variety of other aesthetic shapes could also be employed such as chamfers and radii. In contrast, upper face (96) is asymmetrical relative lower face (91) and lacks shoulder notches, so upper face (96) would interfere with rails (52) if cartridge body (90) were inserted upside-down in cartridge receiving assembly (50). In another instance, the geometry of a proximal face (98) of cartridge body (90) is vertically asymmetrical and thus prevents cartridge body (90) from being inserted upside-down between jaws (51, 56). In this example, proximal face (98) comprises a curved surface that gently transitions to upper face (96), which matches similar geometry in cartridge receiving assembly (50); while the transition to lower face (91) has a tighter radius. Of course, a variety of other asymmetrical aesthetic geometries could also be employed that could contribute to the visual appearance and/or poke-yoke aspects of cartridge body (90).

Arms (93A, 93B) define a generally U-shaped distal end on cartridge body (90). A slot (95) and rotary input (94) are aligned and dimensioned to receive the key (48) while cartridge body (90) is being slid into cartridge receiving assembly (50). When cartridge body (90) is fully seated into cartridge receiving assembly (50), a step (99) aligns with and receives tooth (59) to latch cartridge body (90) in cartridge receiving assembly (50). Key (48) also aligns with rotary input (94), thereby providing a torsional interface that rotationally couples pinion (47) and rotary input (94). In use, the needle (70) exits arm (93A) and enters arm (93B).

Figure 4:
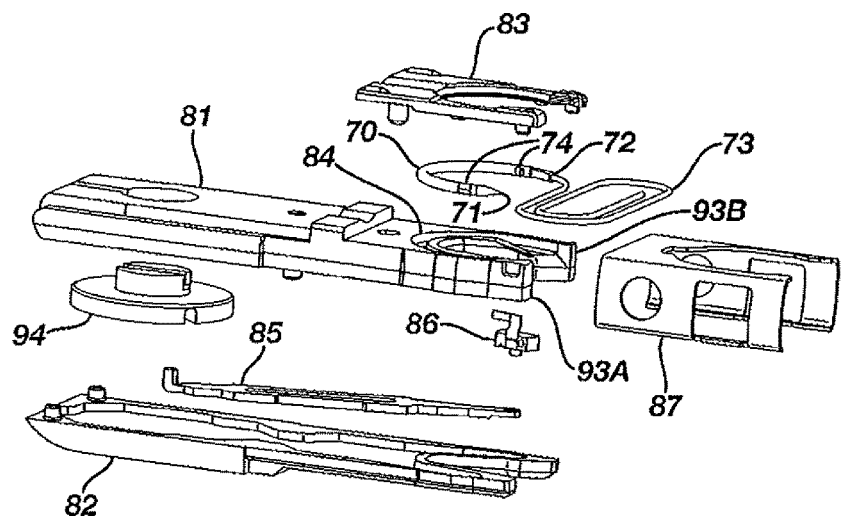
FIG. 4 depicts an exploded view of the cartridge of FIG. 3A.

As shown in FIGS. 3A-4, cartridge body (90) further comprises a lower body (81), an upper body (82), a needle (70), and a needle cover (83). Needle driver (86), rotary input (94), and a link (85) are captured between lower body (81) and upper body (82). Bodies (81, 82) may be attached to one another using a variety of known techniques, including welds, pins, adhesives, and the like to form cartridge body (90). Needle (70) has a leading end (71) and a length of suture (73) extending from the trailing end (72). Needle (70) orbits in a circular path defined by a needle track (84) and between arms (93A, 93B). Needle (70) includes notches (74) that are configured to facilitate engagement between needle driver (86) and needle (70). Needle (70) is captured in needle track (84) by needle cover (83). A cage (87) slides over bodies (81, 82) and needle cover (83) to attach needle cover (83) against lower body (81).

Figure 5A:
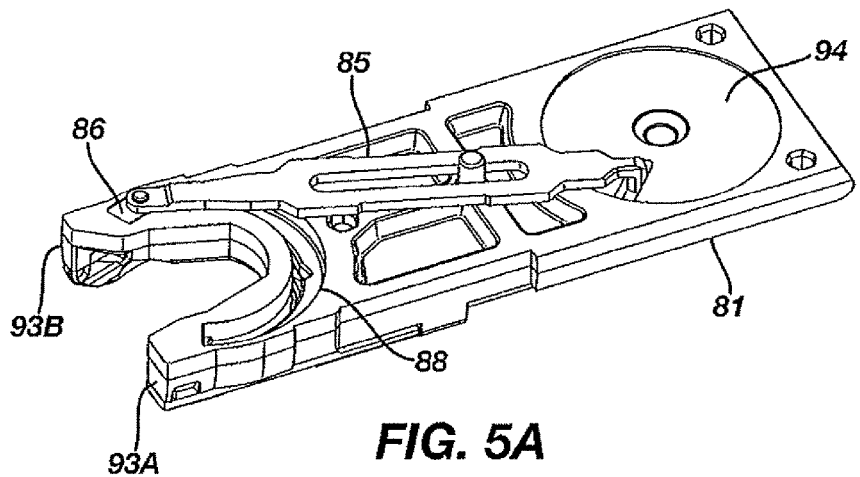
FIG. 5A depicts a perspective view of a drive assembly of the cartridge of FIG. 3A, with the drive assembly at one end of its stroke.
Figure 5B:
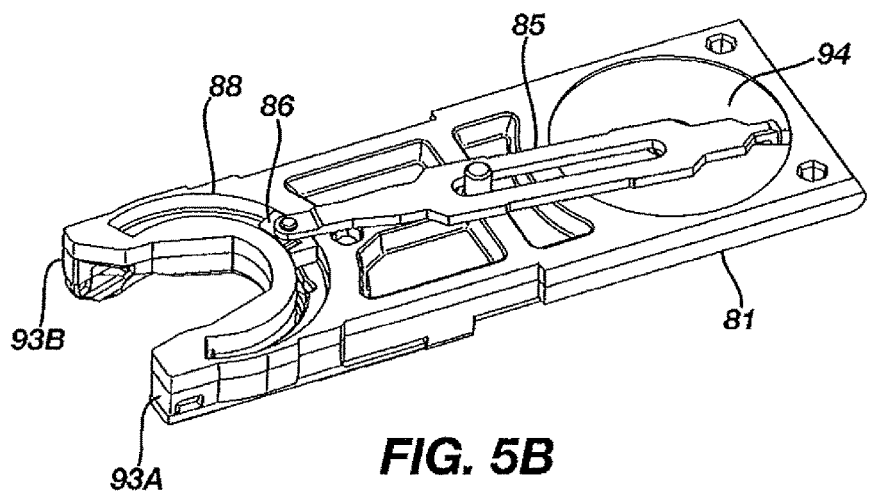
FIG. 5B depicts a perspective view of the drive assembly of FIG. 5A, with the drive assembly at mid-stroke.
Figure 5C:
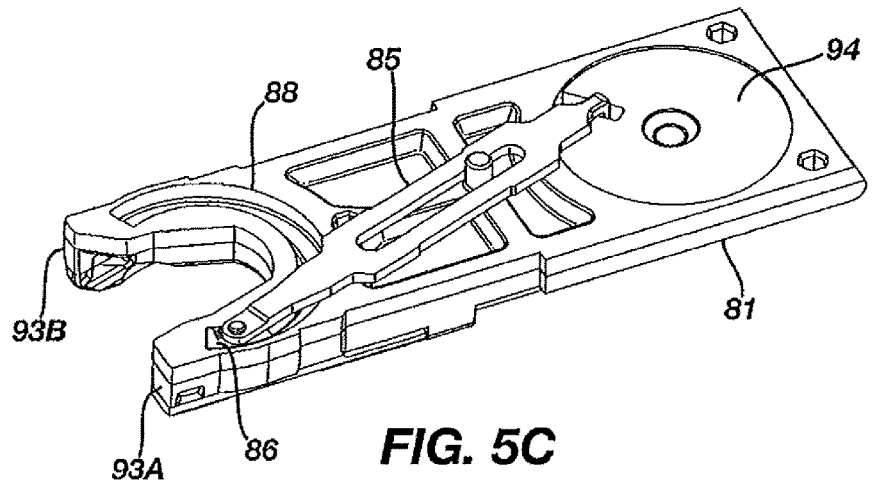
FIG. 5C depicts a perspective view of the drive assembly of FIG. 5A, with the drive assembly at the other end of its stroke.

FIGS. 5A-5C illustrate an example of a drive stroke of the transmission in cartridge body (90) for driving needle (70) in a circular, orbital path. However, it should be understood that needle (70) and suture (73) omitted from FIGS. 5B-5C. Needle driver (86) rides in a carrier track (88) and extends into needle track (84) to engage and drive needle (70). A link (85) connects rotary input (94) to needle driver (86). FIG. 5A shows needle driver (86) positioned at one end of its stroke in carrier track (88). As shown in FIG. 5B, counterclockwise rotation of rotary input (94) will translate needle driver (86) clockwise along carrier track (88), thereby driving needle (70) clockwise. As shown in FIG. 5C, continued counterclockwise rotation of the rotary input (94) will continue to translate needle driver (86) and thereby drive needle (70) clockwise until it reaches the other end of its stroke in carrier track (88). In this example, the drive stroke rotates the needle (70) in its circular path along an angular range of about 180 degrees. For the return stroke, the sequence can be reversed by rotating the rotary input (94) clockwise, which will translate needle driver (86) counterclockwise in carrier track (88). Needle driver (86) is disengaged from needle (70) during the return stroke until needle driver (86) reaches the end of the return stroke. Needle driver (86) will re-engage needle (86) upon completing the return stroke. Thus, a sequence of drive and return strokes will rotate the needle (70) in a circular path.

Figure 6:
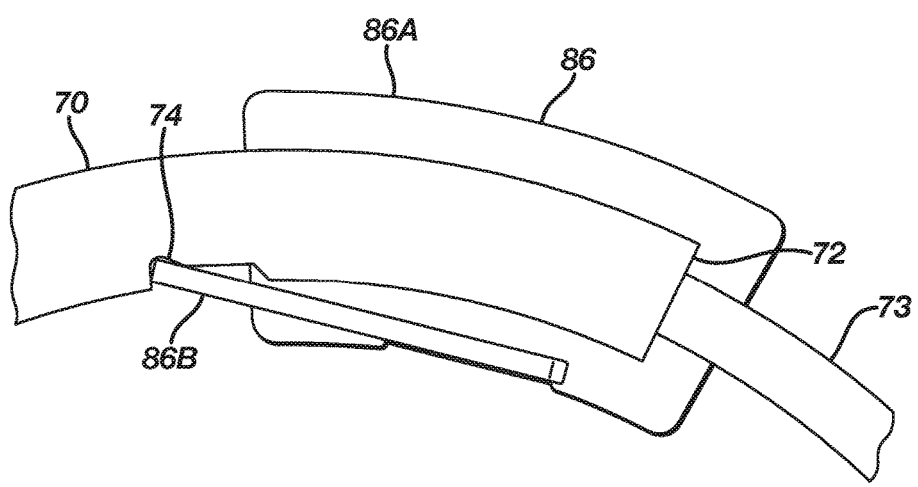
FIG. 6 depicts a partial plan view of a needle driver of the cartridge of FIG. 3A engaging a needle of the cartridge of FIG. 3A.

FIG. 6 illustrates a detailed view of needle driver (86) engaging needle (70). Needle driver (86) comprises a carrier (86A) and a driver (86B). Carrier (86A) is dimensioned to slideably fit in carrier track (88). Driver (86B) is attached to carrier (75) and is operative to engage needle (70) at an oblique angle. Leftward movement of needle driver (86) will cause driver (86B) to engage proximal notch (74) of needle (70) during the drive stroke. When so engaged, needle (70) will slide in needle track (84) in unison with needle driver (86). Due to the oblique angle, rightward movement of needle driver (86) will disengage driver (86B) from proximal notch (74) of needle (70) and slide over the stationary needle (70) during the return stroke.

Referring back to FIGS. 5A-5C, when first input (12) is depressed, closing the trigger, needle driver (86) will be actuated through its drive stroke where it orbits along an angular range of motion at least about 180 degrees counterclockwise to a driven position as shown in FIG. 5C. During the drive stroke, driver (86B) engages proximal notch (74) and will in unison rotate needle (70) about 180 degrees along an orbital path to its extended position. Needle (70) will span across arms (93A, 93B) between exit port (95) and entrance port (97). Tissue interposed between arms (93A, 93B) will be pierced by leading end (71) of needle (70).

When first input (12) is released and the spring return opens the trigger, needle driver (86) reciprocates through its return stroke where it orbits along an angular range of motion about 180 degrees clockwise back to the return position shown in FIG. 5A. During the return stroke, driver (86B) slides over the needle (70). Driver (86B) is then adjacent the distal notch (74). When first input (12) is depressed again closing the trigger, needle driver (86) will again be actuated through its drive stroke where it orbits along an angular range of motion about 180 degrees counterclockwise to the driven position as shown in FIG. 5C. During the drive stroke, driver (86B) engages distal notch (74) and will in unison drive needle (70) orbitally along an angular range of motion about 180 degrees back to its retracted position. Suture (73) will follow needle (70) and be threaded through the pierced tissue.

When first input (12) is again released and the spring return opens the trigger, needle driver (86) again reciprocates through its return stroke where it orbits along an angular range of motion about 180 degrees clockwise back to its returned position as shown in FIG. 5A. During the return stroke, driver (86B) slides over needle (70). Thus, needle (70) is driven in a complete circular path spanning an angular range of 360° in response to first input (12) being actuated twice. The sequence may be repeated as needed by the surgeon to achieve the desired suturing task.

Further details, explanations, examples, and alternative embodiments of surgical suturing devices and subcomponents of the foregoing are disclosed in U.S. Pub. No. 2014/0171970, entitled "Circular Needle Applier with Articulating and Rotating Shaft," published Jun. 19, 2014, issued as U.S. Pat. No. 9,357,998 on Jun. 7, 2016, the disclosure of which is incorporated by reference herein; U.S. patent application Ser. No. 14/297,993, entitled "Jawed Cartridge Receiving Assembly for Needle Cartridge," filed Jun. 6, 2014, issued as U.S. Pat. No. 9,474,522 on Oct. 25, 2016, the disclosure of which is incorporated by reference herein; and U.S. patent application Ser. No. 14/298,038, entitled "Circular Needle Applier with Cleats," filed Jan. 30, 2015, issued as U.S. Pat. No. 9,375,212 on Jun. 28, 2016, the disclosure of which is incorporated by reference herein. It should be understood that such details, explanations, examples, and alternative embodiments may be readily applied to the above-described instrument (10) and subcomponents thereof.

II. Exemplary Endoscopic Surgical Suturing Instrument

In some instances, it may be desirable to attach a variation of instrument (2) to an endoscope. For instance, attaching a variation of instrument (2) to an endoscope may be beneficial when performing, among other surgical procedures, gastric reduction procedures. Examples of suturing instruments attachable to an endoscope are described in U.S. Pat. No. 7,615,060, entitled "Endoscopic Suturing Device," issued Nov. 10, 2009, the disclosure of which is incorporated by reference herein. The following description provides an exemplary variation of instrument (2) that may be attached to an endoscope. Other examples will be apparent to those of ordinary skill in the art according to the teachings herein. It should be understood that the examples described below may function substantially similar to instrument (2) described above. In particular, the surgical suturing instruments described below may be used to suture tissue.

Figure 7:
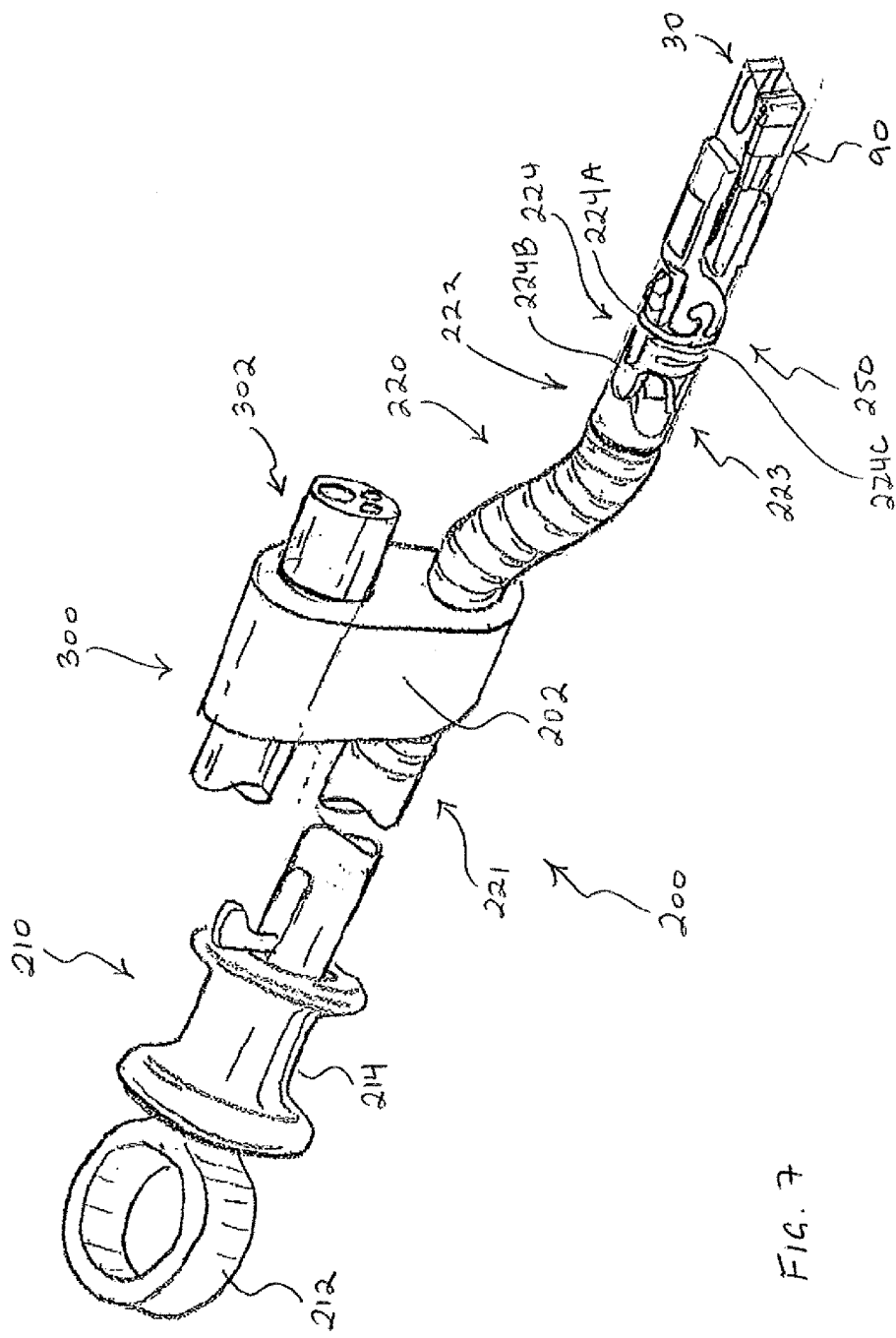
FIG. 7 depicts a perspective view of an exemplary endoscopic surgical suturing instrument coupled with an endoscope.

FIG. 7 illustrates an example of an alternative surgical suturing instrument (200). Instrument (200) comprises a handle assembly (210), a flexible shaft (220), and a cartridge receiving assembly (250), which is operable to receive needle applier cartridge (30) described above. Shaft (220) has a proximal end (221) and a distal end (222). Handle assembly (210) is connected to the proximal end (221) of shaft (220). In this example handle assembly (210) is a syringe grip handle. However, a variety of other handles could also be used, including but not limited to a pistol grip handle, a scissor grip handle, a pencil grip handle, and the like. Handle assembly (210) could also take the form of a robotic interface, such as a DAVINCI puck, or a housing comprising gears or pulleys, servomechanisms, and the like.

Instrument (200) includes a coupler (202). Coupler (202) includes a first through-bore that is shaped and dimensioned to receive the distal end (302) of a commercially available endoscope (300). Coupler (202) further includes a second through-bore that is shaped and dimensioned to receive shaft (220) of instrument (200) so as to couple instrument (200) with endoscope (300) as shown in FIG. 7. Shaft (220) and endoscope (300) are coupled together by coupler (202) in a parallel yet laterally offset relationship. It should be understood that cartridge receiving assembly (250) and cartridge (30) will be positioned such that cartridge receiving assembly (250) and cartridge (30) are within the field of view of an endoscope (300) that is coupled with coupler (202). The operator may thus view operation of cartridge receiving assembly (250) and cartridge (30) via endoscope (300). As will be appreciated by one of ordinary skill in the art, coupling of instrument (200) and endoscope (300) may be beneficial when performing, among other surgical procedures, gastric reduction procedures. Shaft (220) is substantially flexible such that shaft (220) and endoscope (300) may be advanced together along a substantially tortuous path such as a patient's gastrointestinal tract.

Shaft (220) includes cartridge receiving assembly (250) that is configured to releasably hold cartridge body (90). Needle applier cartridge (30) is thus connected to the distal end (222) of shaft (220) via cartridge receiving assembly (250). Cartridge receiving assembly (250) of this example is configured and operable substantially identically to cartridge receiving assembly (50) described above. As described above, needle applier cartridge (30) is operable to rotate an arced needle in a circular path enabling a surgeon to selectively apply sutures. In some alternative versions, needle applier cartridge (30) is integral with shaft (220) and handle assembly (210) as a unitary disposable instrument intended for a single surgical procedure. Needle applier cartridge (30) may also be integral with shaft (220) and handle assembly (210) as a reusable instrument. Optionally, as illustrated here, needle applier cartridge (30) may be provided in cartridge body (90) as described above. In some such versions, shaft (220) and handle assembly (210) may also be disposable or reusable.

Figure 9A:
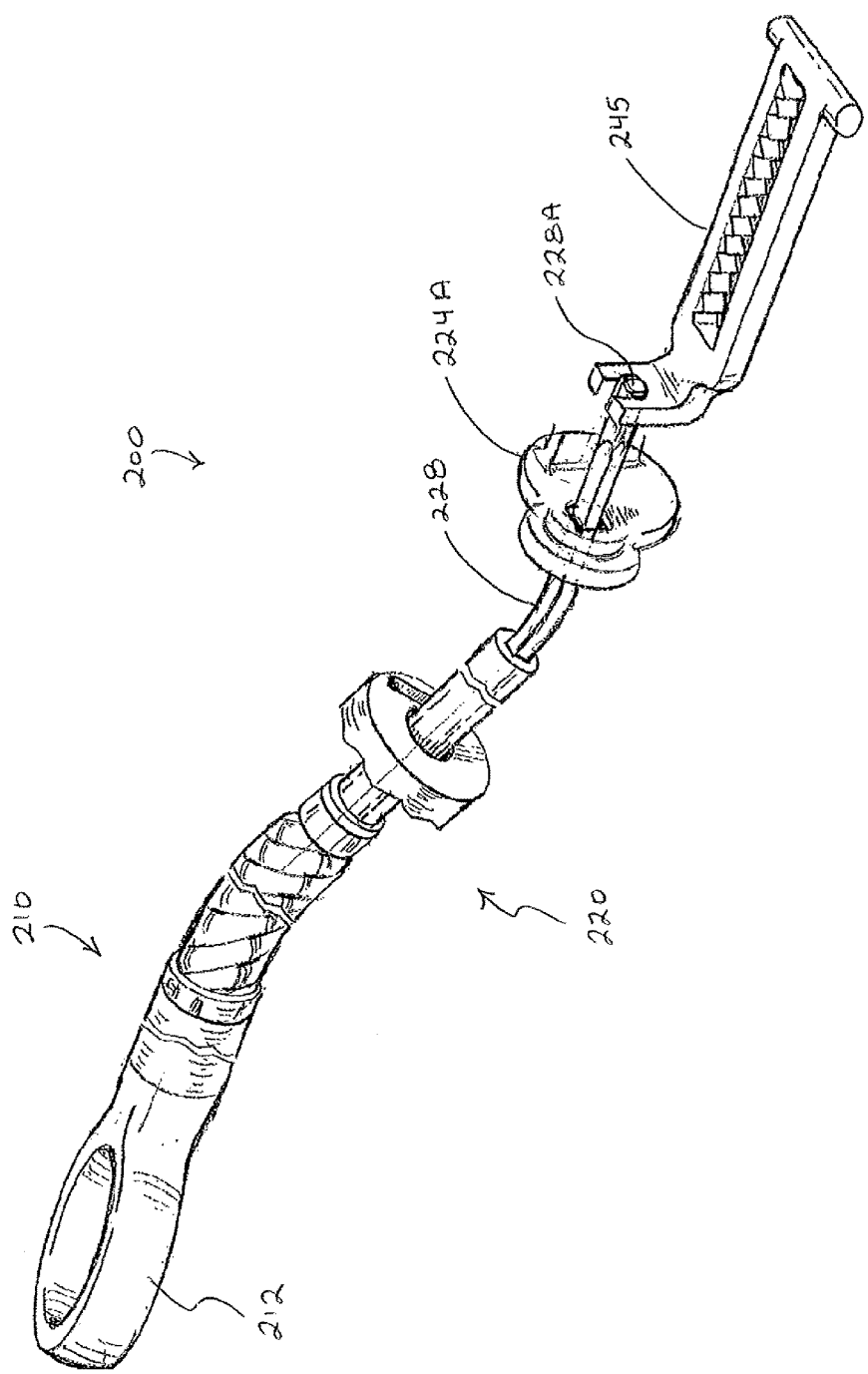
FIG. 9A depicts a perspective view of internal distal head control components of the instrument of FIG. 7, with the distal end of the instrument in a distal longitudinal position and a first rotational position.

Handle assembly (210) comprises a first input (212). In the present example, first input (212) is in the form of a plunger that translates between a proximal and distal position. First input (212) is operable to selectively actuate cartridge receiving assembly (250) to thereby actuate needle applier cartridge (30) by translating from a distal position (FIG. 9A) to a proximal position (FIG. 9B). The plunger may be resiliently biased to return the plunger to its distal position. First input (212) further rotates about a longitudinal axis of handle assembly (210) relative to handle assembly (210) and may further be used to selectively rotate needle applier cartridge (30) about shaft (220). A second input (214), shown here as a rotary knob, may be used to selectively articulate shaft (220). Of course, the number, type, configuration, and operation of inputs (212, 214) may vary.

Distal end (222) of shaft (220) comprises an articulation joint (223) and a rotational bearing (224). Articulation joint (223) defines a pivoting axis for articulation joint (223), enabling cartridge receiving assembly (250) to articulate left and right relative the shaft (220), away from shaft (220). Rotational bearing (224) is positioned distal to articulation joint (223). Bearing (224) includes a circumferential flange (224A) that is captured between a pair of bearing supports (224B, 224C) such that the flange (224A) can rotate relative the bearing supports (224B, 224C) and enable unbounded rotation of cartridge receiving assembly (250) relative shaft (220).

A drive rod (228) extends through shaft (220). In this example, drive rod (228) is flexible. Drive rod (228) extends through articulation joint (223) and through bearing (224). A distal end (228A) of drive rod (228) is fixedly connected to a rack (245). Rack (245) is configured to operate substantially similar to rack (45) described above except for any difference described below. In particular, rack (245) is configured to reciprocate longitudinally within cartridge receiving assembly (250) in response to longitudinal reciprocation of drive rod (228). This longitudinal reciprocation of rack (245) is converted into angular oscillation of rotary input (94) of cartridge body (90), which in turn actuates needle applier cartridge (30) as described above.

Drive rod (228) is operatively connected to first input (212). As shown in FIGS. 9A and 9B, longitudinal actuation of first input (212) between a distal position (FIG. 9A) and a proximal position (FIG. 9B) will impart axial push and pull loads on drive rod (228) to longitudinally reciprocate rack (245) and thereby actuate needle applier cartridge (30). As shown in FIG. 9C, rotational actuation of first input (212) will further impart a rotational load on drive rod (228). Drive rod (228) is operatively keyed with flange (224A) of bearing (224) such that rotation of drive rod (228) causes concurrent rotation of flange (224A), thus rotating cartridge receiving assembly (250) about bearing (224) relative to shaft (220). Accordingly, a single input (212) and a single drive rod (228) are together operate to both actuate needle applier cartridge (30) as well as control distal rotation of needle applier cartridge (30) relative to shaft (220). By consolidating dual functions within a single input (212) and a single drive rod (228), the number of components is reduced, and more space is provided in the shaft (220), which may make the device less expensive to manufacture and easier to clean.

When first input (212) is pulled proximally as shown in FIG. 9B, translating the plunger to the proximal position, needle driver (86) of cartridge body (90) will be actuated through its drive stroke where needle driver (86) orbits along an angular range of motion at least about 180 degrees counterclockwise to the driven position as shown in FIG. 5C. When first input (212) is released and the spring returns the plunger to the distal position (FIG. 9A), needle driver (86) reciprocates through its return stroke where it orbits along an angular range of motion about 180 degrees clockwise back to the return position shown in FIG. 5A. When first input (212) is pulled proximally again to the proximal position (FIG. 9B), needle driver (86) will again be actuated through its drive stroke where needle driver (86) orbits along an angular range of motion about 180 degrees counterclockwise to the driven position as shown in FIG. 5C. When first input (212) is again released and the spring returns the plunger to the distal position (FIG. 9A), needle driver (86) again reciprocates through its return stroke where needle driver (86) orbits along an angular range of motion about 180 degrees clockwise back to its returned position as shown in FIG. 5A. Thus, needle (70) is driven in a complete circular path spanning an angular range of 360° in response to first input (212) being actuated twice. The sequence may be repeated as needed by the surgeon to achieve the desired suturing task.

Figure 10:
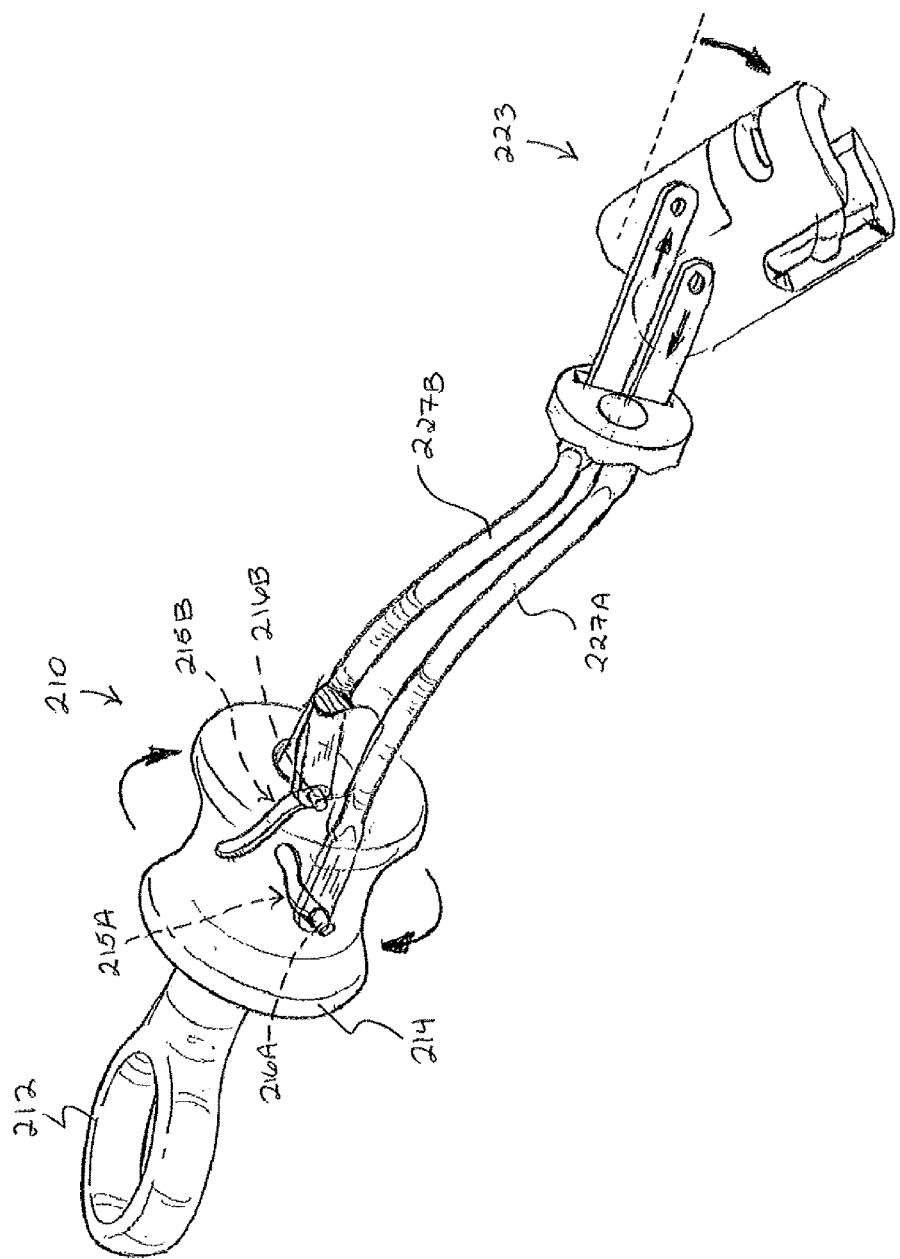
FIG. 10 depicts a perspective view of internal articulation control components of the instrument of FIG. 7.

Rotary knob (214) is operable to selectively articulate joint (223). As shown in FIG. 10, shaft (220) includes a pair of articulation rods (227A, 227B) slidably disposed within and extend through shaft (220). Rods (227A, 227B) are operably connected to articulation joint (223). Rods (227A, 227B) are operatively connected to rotary knob (214) to opposingly push and pull rods (227A, 227B). In other words, rotary knob (214) is operable to drive rods (227A, 227B) at the same time in opposite longitudinal directions, such that rod (227A) will translate distally while rod (227B) translates proximally; and such that rod (227B) will translate distally while rod (227A) translates proximally. The simultaneous push and pull action will in turn articulate cartridge receiving assembly (250) about joint (223) relative to shaft (220). In particular, rotary knob (214) includes a pair of cam slots (215A, 215B) formed in opposing sides of an interior surface of rotary knob (214). Rods (227A, 227B) are operably secured within cam slots (215A, 215B) via pins (216A, 216B). As shown in FIGS. 11A-11C, cam slots (215A, 215B) are shaped such that as rotary knob (214) is rotated about a longitudinal axis extending through knob (214), rotary knob (214) is operable to drive rods (227A, 227B) at the same time in opposite longitudinal directions to thereby articulate cartridge receiving assembly (250) about joint (223) relative to shaft (220).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) a body, wherein the body comprises at least one user input feature; (b) a shaft, wherein the shaft comprises a distal end and a proximal end; (c) a needle applier located at the distal end of the shaft, wherein the needle applier comprises: (i) a needle, and (ii) a drive assembly coupled to the needle, wherein the drive assembly is configured to drive the needle along an orbital path about a rotation axis that is transverse to the longitudinal axis, in response to an actuation of the user input feature; and (d) a coupler, wherein the coupler is operable to selectively couple the surgical instrument with an endoscope.

Example 2

The apparatus of Example 1, wherein the at least one user input feature comprises a first user input feature, wherein the first user input feature is configured to actuate to thereby drive actuation of the drive assembly.

Example 3

The apparatus of Example 2, wherein the first user input feature is configured to actuate between a between a proximal position and a distal position.

Example 4

The apparatus of Example 3, wherein the first user input is configured to translate proximally to thereby actuate the needle drive assembly.

Example 5

The apparatus of any one or more of Examples 3 through 4, wherein the first user input feature comprises a plunger.

Example 6

The apparatus of any one or more of Examples 2 through 5, wherein the distal end of the shaft is rotatable relative to the shaft so as to cause rotation of the needle applier relative to the shaft.

Example 7

The apparatus of Example 6, wherein the first user input feature is configured to actuate to thereby drive rotation of the distal end of the shaft.

Example 8

The apparatus of Example 7, wherein the first user input feature is configured to actuate between rotational positions relative to the body.

Example 9

The apparatus of any one or more of Examples 2 through 8, wherein the shaft comprises an articulation joint, wherein the shaft is operable to articulate at the articulation joint to thereby deflect the needle applier toward and away from the shaft.

Example 10

The apparatus of Example 9, wherein the at least one user input feature further comprises a second user input feature.

Example 11

The apparatus of Example 10, wherein the second user input feature is configured to actuate to thereby drive articulation of the shaft.

Example 12

The apparatus of Example 11, wherein the second user input feature is configured to actuate between rotational positions relative to the body.

Example 13

The apparatus of any one or more of Examples 11 through 12, wherein second user input feature comprises a rotary knob.

Example 14

The apparatus of Example 13, wherein the shaft comprises a pair of articulation rods, wherein the rotary knob includes a pair of cam slots, wherein the articulation rods are operably coupled within the cam slots such that rotation of the rotary knob causes opposing movement of the articulation rods.

Example 15

The apparatus of any one or more of Examples 1 through 14, wherein the shaft is flexible.

Example 16

The apparatus of any one or more of Examples 1 through 15, wherein the coupler comprises a first bore and a second bore, wherein the first bore is configured to receive the endoscope, wherein the second bore is configured to receive the shaft.

Example 17

A surgical instrument comprising: (a) a body, wherein the body comprises: (i) a first user input feature, and (ii) a second user input feature; (b) a flexible shaft, wherein the flexible shaft comprises: (i) a distal end, (ii) a proximal end, and (iii) an articulation joint; (c) a needle applier located at the distal end of the shaft, wherein the needle applier further comprises: (i) a needle, and (ii) a drive assembly coupled to the needle, wherein the drive assembly is configured to drive the needle along an orbital path about a rotation axis that is transverse to the longitudinal axis, in response to an actuation of the first user input feature; and (d) a coupler, wherein the coupler is operable to selectively couple the surgical instrument with an endoscope; wherein the shaft is operable to articulate at the articulation joint to thereby deflect the needle applier toward and away from the shaft in response to actuation of the second user input feature.

Example 18

The apparatus of Example 17, wherein the distal end of the shaft is rotatable relative to the shaft so as to cause rotation of the needle applier relative to the shaft.

Example 19

The apparatus of Example 18, wherein the first user input feature is further configured to actuate to thereby drive rotation of the distal end of the shaft.

Example 20

A surgical instrument comprising: (a) a body, wherein the body comprises at least one user input feature; (b) a shaft, wherein the shaft comprises a distal end and a proximal end; (c) a needle applier, wherein the needle applier is located at the distal end of the shaft, wherein the needle applier comprises: (i) a needle, and (ii) a drive assembly coupled to the needle, wherein the drive assembly is configured to drive the needle along an orbital path about a rotation axis that is transverse to the longitudinal axis, in response to an actuation of the user input feature; and (d) a coupler, wherein the coupler is operable to selectively couple the surgical instrument with an endoscope; wherein the distal end of the shaft is rotatable relative to the shaft so as to cause rotation of the needle applier relative to the shaft, wherein the at least one user input feature is configured to actuate to thereby drive actuation of the drive assembly, wherein the at least one user input feature is further configured to actuate to thereby drive rotation of distal end of the shaft.

IV. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
   (a) a body, wherein the body comprises:
      (i) a first actuating body, and
      (ii) a rotary knob defining a cam slot;
   (b) a shaft, wherein the shaft comprises:
      (i) a distal end defining a longitudinal axis, wherein the distal end comprises an articulation joint, wherein the articulation joint terminates in a pair of bearing supports,
      (ii) a proximal end, and
      (iii) an articulation rod slidably coupled with the rotary knob via a pin that is slidably disposed within the cam slot;
   (c) a needle applier coupled with the distal end of the shaft at the articulation joint, wherein the rotary knob is configured to rotate in order to drive the pin slidably along the cam slot to thereby actuate the articulation rod to deflect the needle applier about the articulation joint, wherein the needle applier comprises:
      (i) a needle,
      (ii) a proximal circumferential flange captured between the pair of bearing supports, and
      (iii) a drive assembly coupled to the needle, wherein the drive assembly is configured to drive the needle along an orbital path about a rotation axis that is transverse to the longitudinal axis, in response to an actuation of the first actuating body, wherein the first actuating body is configured to rotate the needle applier about the longitudinal axis relative to the articulation joint such that the proximal circumferential flange rotates within the pair of bearing supports; and
   (d) a coupler, wherein the coupler is operable to selectively couple the surgical instrument with an endoscope.

2. The surgical instrument according to claim 1, wherein the first actuating body is configured to actuate between a proximal position and a distal position.

3. The surgical instrument according to claim 2, wherein the first actuating body is configured to translate proximally to thereby actuate the needle drive assembly.

4. The surgical instrument according to claim 2, wherein the first actuating body comprises a plunger.

5. The surgical instrument according to claim 1, wherein the distal end of the shaft is rotatable relative to a proximal end of the shaft so as to cause rotation of the needle applier relative to the proximal end of the shaft.

6. The surgical instrument according to claim 5, wherein the first actuating body is configured to actuate to thereby drive rotation of the distal end of the shaft.

7. The surgical instrument according to claim 6, wherein the first actuating body is configured to actuate between rotational positions relative to the body.

8. The surgical instrument according to claim 1, wherein the shaft is flexible.

9. The surgical instrument according to claim 1, wherein the coupler comprises a first bore and a second bore, wherein the first bore is configured to receive the endoscope, wherein the second bore is configured to receive the shaft.

10. A surgical instrument comprising:
(a) a body, wherein the body comprises:
(i) a first user input feature, and
(ii) a rotary knob defining a cam slot;
(b) a flexible shaft, wherein the flexible shaft comprises:
(i) a distal end defining a longitudinal axis,
(ii) a proximal end,
(iii) an articulation joint comprising a pair of bearing supports, and
(iv) an articulation rod slidably coupled with the cam slot of the rotary knob via a pin that is slidably disposed within the cam slot;
(c) a needle applier comprising a circumferential flange captured between the pair of bearing supports, wherein the needle applier is located at the distal end of the shaft, wherein the first user input feature is configured to rotate the circumferential flange of the needle applier about the longitudinal axis relative to the pair of bearing supports of the articulation joint, wherein the needle applier further comprises:
(i) a needle, and
(ii) a drive assembly coupled to the needle, wherein the drive assembly is configured to drive the needle along an orbital path about a rotation axis that is transverse to the longitudinal axis, in response to an actuation of the first user input feature; and
(d) a coupler, wherein the coupler is operable to selectively couple the surgical instrument with an endoscope;
wherein the rotary knob is operable to rotate in order to drive the pin slidably along the cam slot to thereby actuate the articulation rod, thereby deflecting the needle applier toward and away from the shaft in response to actuation of the rotary knob.

11. The surgical instrument according to claim 10, wherein the distal end of the shaft is rotatable relative to a proximal end of the shaft so as to cause rotation of the needle applier relative to the proximal end of the shaft.

12. The surgical instrument according to claim 11, wherein the first user input feature is further configured to drive rotation of the distal end of the shaft.

13. A surgical instrument comprising:
(a) a body, wherein the body comprises:
(i) a first input drive, and
(ii) a rotary knob defining a cam slot;
(b) a shaft, wherein the shaft comprises:
(i) a distal end defining a longitudinal axis, wherein the distal end comprises an articulation joint and a pair of bearing supports,
(ii) a proximal end, and
(iii) an articulation rod slidably coupled with the cam slot of the rotary knob via a pin;
(c) a needle applier comprising a proximal circumferential flange captured between the pair of bearing supports, wherein the needle applier is located at the distal end of the shaft, wherein the rotary knob is configured to rotate in order to drive the pin slidably along the cam slot to thereby actuate the articulation rod in order to deflect the needle applier relative to the shaft, wherein the first input drive is configured to rotate the needle applier about the longitudinal axis relative to the articulation joint such that the proximal circumferential flange rotates within the pair of bearing supports, wherein the needle applier comprises:
(i) a needle, and
(ii) a drive assembly coupled to the needle, wherein the drive assembly is configured to drive the needle along an orbital path about a rotation axis that is transverse to the longitudinal axis; and
(d) a coupler, wherein the coupler is operable to selectively couple the surgical instrument with an endoscope.

14. The surgical instrument of claim 13, wherein the needle applier is coupled with the distal end of the shaft at an articulation joint.

15. The surgical instrument of claim 13, wherein the shaft is flexible.

16. The surgical instrument of claim 13, wherein the distal end of the shaft is rotatable relative to a proximal end of the shaft so as to cause rotation of the needle applier relative to the proximal end of the shaft.

* * * * *